United States Patent
Vermeulen et al.

(10) Patent No.: US 12,245,869 B2
(45) Date of Patent: Mar. 11, 2025

(54) WAVELENGTH AND BANDWIDTH SELECTION FOR DIFFUSE REFLECTIVE SPECTROSCOPY BASED GINGIVITIS DETECTION

(71) Applicant: KONINKLIJKE PHILIPS N.V., Eindhoven (NL)

(72) Inventors: Olaf Thomas Johan Antonie Vermeulen, Oss (NL); Steven Charles Deane, Cambridge (GB); Lucas Petrus Henricus Scheffers, Utrecht (NL); Estelle Julie Dorothée Bernard-Fichet, Cambridge (GB); Adrianus Wilhelmus Dionisius Maria Van Den Bijgaart, Helvoirt (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1036 days.

(21) Appl. No.: 17/275,226

(22) PCT Filed: Sep. 9, 2019

(86) PCT No.: PCT/EP2019/073912
§ 371 (c)(1),
(2) Date: Mar. 11, 2021

(87) PCT Pub. No.: WO2020/053110
PCT Pub. Date: Mar. 19, 2020

(65) Prior Publication Data
US 2022/0047206 A1 Feb. 17, 2022

Related U.S. Application Data

(60) Provisional application No. 62/729,466, filed on Sep. 11, 2018.

(51) Int. Cl.
*A61B 5/00* (2006.01)

(52) U.S. Cl.
CPC .......... *A61B 5/4552* (2013.01); *A61B 5/0075* (2013.01); *A61B 5/0088* (2013.01)

(58) Field of Classification Search
None
See application file for complete search history.

(56) References Cited

U.S. PATENT DOCUMENTS

| 5,413,100 A | 5/1995 | Barthelemy et al. |
| 5,467,767 A * | 11/1995 | Alfano ............... G01N 21/6408 600/476 |

(Continued)

FOREIGN PATENT DOCUMENTS

JP 2018051304 A 4/2018

OTHER PUBLICATIONS

International Search Report and Written Opinion, International Application No. PCT/EP2019/073912, Mailed on Nov. 13, 2019.

(Continued)

*Primary Examiner* — Patricia J Park

(57) ABSTRACT

A system (100) for detecting tissue inflammation, and gingivitis specifically, including a light emitter (102); a diffuse reflective spectroscopy probe (107) having a source-detector distance between 300 μm-2000 μm; and a plurality of detectors (106, 108, 112) configured to detect: a first wavelength that is less than 615 nm and having a first bandwidth; and second and third wavelengths that are equal to or greater than 615 nm and have second and third bandwidths, respectively, wherein the second or third bandwidth is greater than the first bandwidth.

12 Claims, 3 Drawing Sheets

(56) References Cited

U.S. PATENT DOCUMENTS

| | | | |
|---|---|---|---|
| 5,570,182 A | | 10/1996 | Nathel et al. |
| 5,818,048 A | * | 10/1998 | Sodickson ......... G01N 21/4795 |
| | | | 250/343 |
| 9,554,738 B1 | * | 1/2017 | Gulati .................. A61B 5/0075 |
| 2002/0103439 A1 | * | 8/2002 | Zeng ..................... G01J 3/0289 |
| | | | 600/476 |
| 2004/0064053 A1 | | 4/2004 | Chang et al. |
| 2010/0280392 A1 | | 11/2010 | Liu et al. |
| 2015/0173618 A1 | | 6/2015 | Kusukame |
| 2016/0038076 A1 | | 2/2016 | Muller et al. |
| 2016/0270716 A1 | * | 9/2016 | Guan ............... A61B 1/000094 |
| 2018/0214057 A1 | * | 8/2018 | Schultz .................. A61B 5/742 |

OTHER PUBLICATIONS

Zakian, C. et al., "In vivo quantification of gingival inflammation using spectral imaging", Journal of Biomedical Optics, vol. 13, No. 5, Jan. 2008.

Hanioka, T. et al., "Hemoglobin concentration and oxygen saturation of clinically healthy and inflamed gingiva in human subjects", Journal of Periodontal Research, vol. 25, No. 2, Mar. 1990.

Prasanth, C. et al., "Non-invasive detection of periodontal disease using diffuse reflectance spectroscopy: a clinical study", Proceedings of SPIE, vol. 8230, Feb. 2012.

Lobene, R. et al., "A modified gingival index for use in clinical trials", Clin. Prev. Dent., 8:3-6, 1986.

Zonios G, Dimou A (2006) Modeling diffuse reflectance from semi-infinite turbid media: application to the study of skin optical properties. Vol. 14, No. 19 / Optics Express 8661.

Fredriksson, Larsson, and Stromberg (2012): Inverse Monte Carlo method in a multilayered tissue model for diffuse reflectance spectroscopy. Journal of Biomedical Optics 17(4), 047004.

Hennessy et al. (2013): Monte Carlo lookup table-based inverse model for extracting optical properties from tissue-simulating phantoms using diffuse reflectance spectroscopy. J Biomed Opt. Mar. 2013; 18(3): 037003.

* cited by examiner

WAVELENGTH AND BANDWIDTH SELECTION FOR DIFFUSE REFLECTIVE SPECTROSCOPY BASED GINGIVITIS DETECTION

This application is the U.S. National Phase application under 35 U.S.C. § 371 of International Application No. PCT/EP2019/073912, filed on 9 Sep. 2019, which claims the benefit of U.S. Provisional Application No. 62/729,466, filed 11 Sep. 2018. These applications are hereby incorporated by reference herein.

FIELD OF THE INVENTION

The present disclosure is directed generally to oral healthcare systems for detecting the presence of tissue inflammation, and gingivitis specifically, using an optimized wavelength selection for spectral analysis.

BACKGROUND

Gingivitis detection using diffuse reflective spectroscopy (DRS) is currently performed with small, angled probes configured around one or more optical fibers which transport light due to the limited space in an oral cavity. Such small probes are useful for measuring at the interproximal areas where gingivitis commonly originates. However, when in contact, such small probes can exert a large pressure on the tissue, pushing away the blood and thereby disrupting the DRS measurement of blood properties. Thus, DRS measurements are preferably taken in non-contact mode and the required non-contact mode leads to detecting specular reflected light in addition to the desired diffuse reflected component. Since diffuse reflected light (i.e., light propagated through tissue) is highly attenuated, these specular components can become relatively large.

Due to the different chromophores in gingival tissue, the spectral properties of diffuse reflected light differs from those of the source light: The influence of hemoglobin absorption is apparent, as is the scattering component, which is the component that enables the diffuse reflectance (i.e. without it, no light would be diffusely reflected/returned) and the absorption component due to melanin, which is one of the main absorbing chromophores in gingival tissue. The other main chromophores are carotene and hemoglobin: especially oxygenated and deoxygenated.

In principle all tissue optical properties can be extracted from the measured DRS spectrum. This can be done using inverse models or Look-Up-Tables (LUT) generated using Monte Carlo simulations. However, these approaches are not appropriate for consumer products because of the required processing power and time and especially the number of sampling-wavelengths required.

To extract hemoglobin concentrations out of a DRS spectrum it is common to use one or more isosbestic wavelengths, e.g., those at approximately 584 nm and 800 nm. However, near-infrared (NIR) wavelengths are normally not generated by lighting LEDs because such wavelengths cannot be seen. Accordingly, output at >780 nm of normal lighting LEDs is extremely low or zero.

Accordingly, there is a continued need in the art for inventive oral healthcare systems and methods for enabling accurate detection of tissue inflammation, and gingivitis specifically, using a minimum number of wavelengths and commercially available phosphor-converted (PC) light-emitting diodes (LEDs).

SUMMARY OF THE INVENTION

The present disclosure is directed to inventive systems and methods for diffuse reflective spectroscopy-based gingivitis detection using lighting light-emitting diodes. Various embodiments and implementations herein are directed to gingivitis detection systems including an oral healthcare device using commercially available light-emitting diodes (LEDs) and an optimized minimum number of wavelengths, which still enable accurate gingivitis detection. The oral healthcare device includes one or more light emitters using commercially available lighting LEDs, a DRS probe, and detectors using the optimized minimum number of wavelengths.

Generally, in one aspect, a system for detecting tissue inflammation is provided. The system includes a light emitter; a diffuse reflective spectroscopy probe having a source-detector distance between 300 μm-2000 μm; and a plurality of detectors configured to detect: a first wavelength that is less than 615 nm and having a first bandwidth; and second and third wavelengths that are equal to or greater than 615 nm and have second and third bandwidths, respectively, wherein the second or third bandwidth is greater than the first bandwidth.

In various embodiments, the light emitter is configured to deliver light to gingival tissue and the plurality of detectors is configured to detect diffuse reflected light from the gingival tissue.

In one embodiment, the system further includes a spectral analysis unit configured to receive and analyze detected diffuse reflected light, the spectral analysis unit including a splitter configured to distribute the detected light over the plurality of detectors.

In various embodiments, the system further includes a controller having an inflammation detection unit, the controller configured to receive input from each of the plurality of detectors for detecting tissue inflammation.

In one embodiment, the second or third bandwidth is at least 50% greater than the first bandwidth.

In one embodiment, the second or third bandwidth is 100% greater than the first bandwidth.

In one embodiment, the second or third bandwidth is 100%-400% greater than the first bandwidth.

In one embodiment, the second and third bandwidths are greater than the first bandwidth.

Generally, in another aspect, a system for detecting tissue inflammation is provided. The system includes a plurality of light emitters; a diffuse reflective spectroscopy probe having a source-detector distance between 300 μm-2000 μm; and a detector configured to detect: a first wavelength that is less than 615 nm and having a first bandwidth; and second and third wavelengths that are equal to or greater than 615 nm and have second and third bandwidths, respectively, wherein the second or third bandwidth is greater than the first bandwidth.

In various embodiments, the plurality of light emitters is configured to deliver light to gingival tissue and the detector is configured to detect diffuse reflected light from the gingival tissue.

In one embodiment, the plurality of light emitters are configured to deliver light to a light combiner which is configured to combine the emitted light and deliver the combined light to gingival tissue.

In one embodiment, the second or third bandwidth is at least 50% greater than the first bandwidth.

In one embodiment, the second or third bandwidth is 100% greater than the first bandwidth.

In one embodiment, the second or third bandwidth is 100%-400% greater than the first bandwidth.

In one embodiment, the second and third bandwidths are greater than the first bandwidth.

As used herein for purposes of the present disclosure, the term "controller" is used generally to describe various apparatus relating to the operation of an imaging apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of systems and methods for improved detection of tissue inflammation, and gingivitis specifically, using commercially available light-emitting diodes (LEDs) and diffuse reflective spectroscopy (DRS). More generally, Applicant has recognized and appreciated that it would be beneficial to provide an optimized wavelength selection for DRS-based gingivitis detection using wavelengths within the visible spectrum. Accordingly, the systems and methods described or otherwise envisioned herein provide an oral healthcare device configured to obtain measurements of gingival tissue. The oral healthcare device includes a light emitter using commercially available lighting LEDs, a DRS probe, and detectors for spectral analysis.

The embodiments and implementations disclosed or otherwise envisioned herein can be utilized with any suitable oral healthcare device. Examples of suitable oral healthcare devices include a toothbrush, a flossing device, an oral irrigator, a tongue cleaner, or other personal care device. However, the disclosure is not limited to these oral healthcare devices, and thus the disclosure and embodiments disclosed herein can encompass any oral healthcare device.

Gingivitis, which is an inflammation of the gums, characterized by swollen gums, edema, and redness, is primarily caused by plaque build-up, mostly in the gingival sulcus (pockets). Such gum disease is typically found in areas that are hard to reach, such as interproximal areas between the teeth, and around the back teeth.

Indeed, it is estimated that 50%-70% of the adult population is affected by gingivitis. However, consumers are often unable to detect early signs of gingivitis. Typically, gingivitis progresses until individuals notice their gums bleeding easily when brushing their teeth. Accordingly, gingivitis may only be detected when the disease is already advanced and significantly harder to treat. Although gingivitis is readily reversed by improved oral hygiene, as gingivitis can propagate to irreversible periodontitis it is important to keep good oral health and detect gingivitis as soon as possible.

Gingivitis may be visually diagnosed by detecting reddening and swelling of the gingiva. (See RR. Lobene, et al., "A modified gingival index for use in clinical trials", Clin. Prev. Dent. 8:3-6, (1986) describing a non-contact gingivitis index, based on reddening and inflammation of the gingiva). However, this has limited sensitivity and is highly dependent on the color rendering index of the light-source used. Thus, modern phosphor-converted LEDs can have a low CRI resulting in poor visual judgments.

Figure 1:
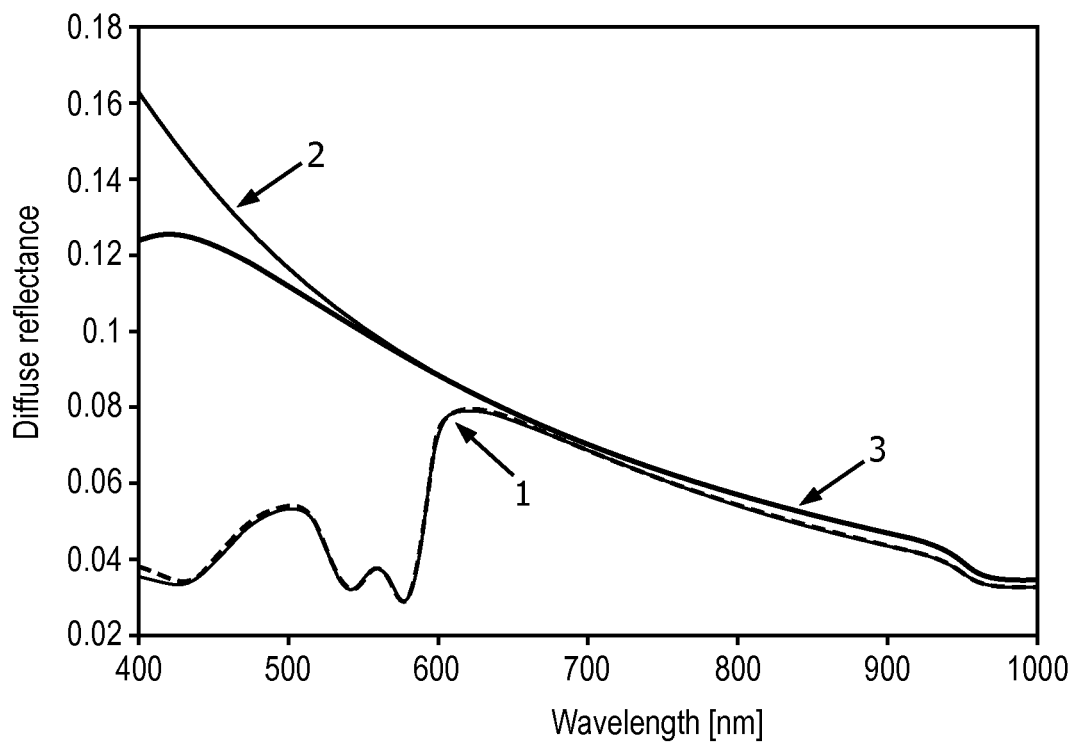
FIG. 1 is a graph representing a diffuse reflective spectroscopy spectrum measured from a healthy gingiva.

FIG. 1 shows an example of a diffuse reflective spectroscopy (DRS) spectrum measured from a healthy gingiva 1, the bottom (dotted) line in the chart, which shows the measurement that includes hemoglobin (blood) and melanin. Also shown are the scattering component 2, the top line in the chart, which is the component that enables the diffuse reflectance (i.e. without it, no light would be diffusely reflected/returned). Line 3 (the middle line in the chart) shows the absorption component due to melanin 3 which is one of the main absorbing chromophores in gingival tissue. The hemoglobin-dominated region is best suited for determining an amount of the DRS signal originating from blood.

Figure 2:
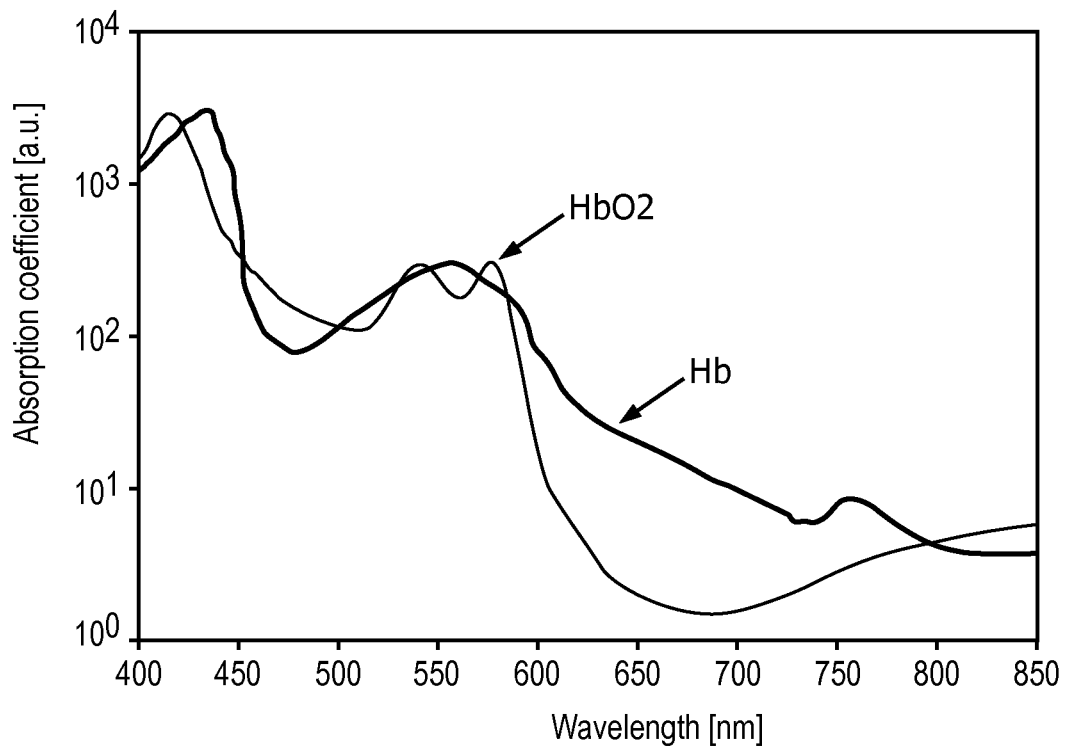
FIG. 2 is a graph representing absorption spectra of oxygenated and deoxygenated hemoglobin.

The influence of hemoglobin absorption is apparent when looking at FIG. 2. Some of the other main absorbing chromophores are hemoglobin: especially oxy-hemoglobin (HbO2) and deoxy-hemoglobin (Hb). The absorption spectra of these two chromophores are clearly shown in FIG. 2.

The reddening of the gingiva is an acute inflammatory response to bacterial biofilm toxins from plaque in the gingivae sulcus or regions along the gum line. This inflammatory response in the short term causes vasodilation, where smooth muscle cells in the arterioles relax, and widen the blood vessels to increase blood supply to the capillary bed. This gives the reddening of the gingiva, and can give a small temperature increase, which is difficult to measure. In addition, the capillaries become more permeable, which results in increased fluid loss from the capillaries to the interstitial spaces, resulting in the swelling of the gums. If the inflammation is chronic, then additional reddening occurs by increased vascularization of the tissue, where additional capillaries may be formed to cope with the additional blood demands of the tissue.

Figure 3:
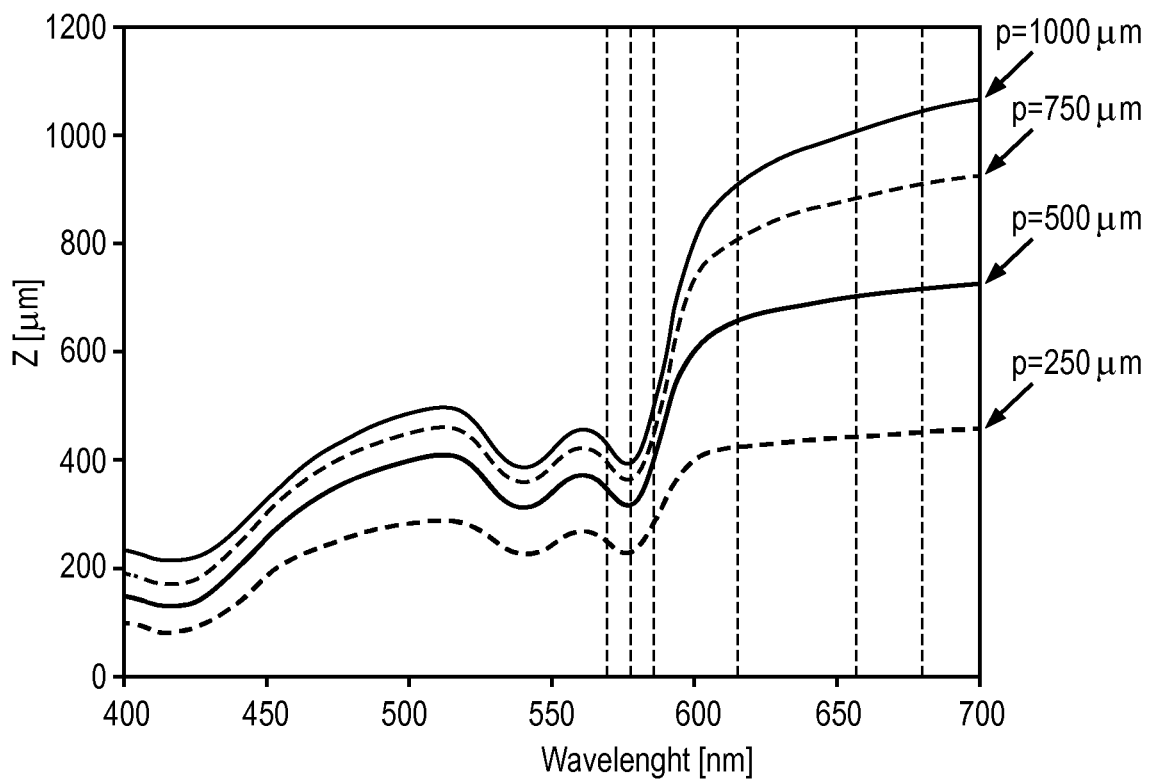
FIG. 3 is a graph representing wavelength-dependent sampling depth using 200 μm fibers for different source-detector distances.

These factors enable detection of gingivitis based on diffuse reflective spectroscopy (DRS). DRS is an optical method that involves emitting, for example, white light towards a target and analyzing spectral properties of the diffuse (rather than specular) reflected light. DRS probe configurations consist of one source fiber next to one detection fiber, one central source fiber surrounded by a plurality of detection fibers, or a single fiber functioning as source and detector simultaneously. An important property of the probe is the source-detection separation because it influences the sampling depth of the probe (i.e., from how deep in the tissue the measured light originates). To detect gingivitis, an average diffuse reflective spectroscopy sampling depth that is greater than 250 μm is required. To obtain such an average, a minimum source-detector distance of approximately 300 μm is required, depending on wavelength. However, such sampling depth cannot be achieved with blue light due to the high absorption in hemoglobin. FIG. 3 shows wavelength-dependent sampling depths (250 μm to 1000 μm) for different source-detector distances. Moreover, all gingivae are not equal and in some individuals the sampling depth may need to be deeper, thus, different wavelength(s) and/or probe designs may be required.

A particular goal of utilization of certain embodiments of the present disclosure is to enable accurate gingivitis detection with diffuse reflective spectroscopy signals using a minimum number of wavelengths and commercially available phosphor-converted (PC) light-emitting diodes (LEDs).

Figure 4:
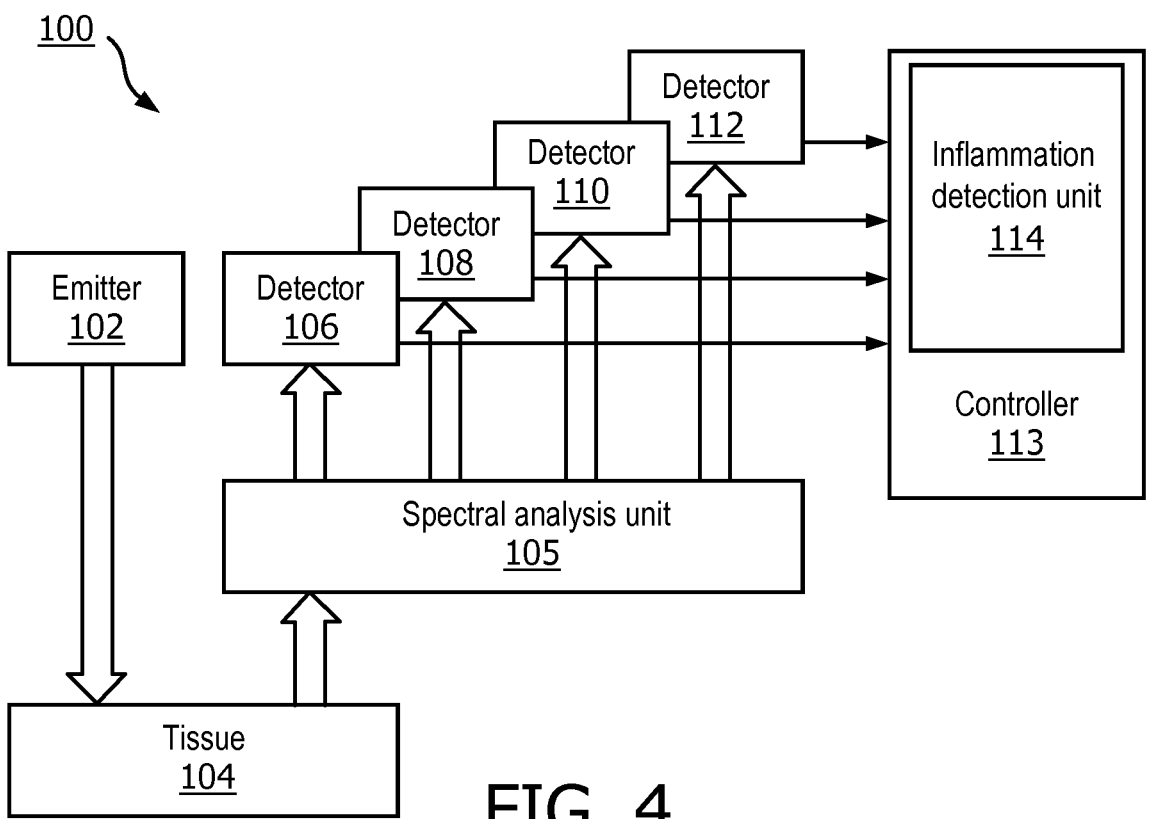
FIG. 4 is a schematic representation of a system for detecting tissue inflammation, in accordance with an embodiment.
Figure 6:
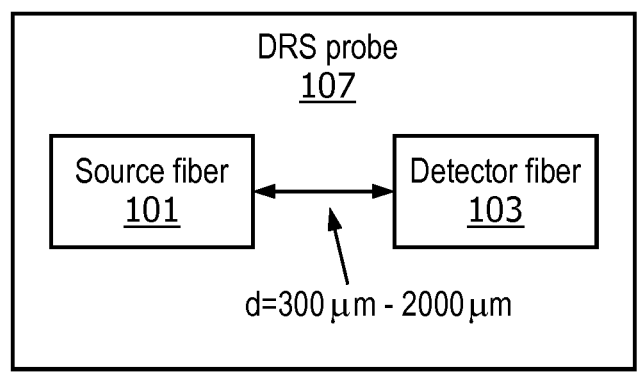
FIG. 6 is a schematic representation of a diffuse reflective spectroscopy probe, in accordance with an embodiment.

Referring to FIG. 4, in one embodiment, is a tissue inflammation detection system 100. System 100 includes a light emitter 102 using commercially available lighting LEDs. The inventive systems described herein use commercially available lighting LEDs because they are inexpensive and efficient. Thus, the available wavelength range is typically from to 500 nm-780 nm. System 100 also includes a diffuse reflective spectroscopy (DRS) probe 107 (shown in FIG. 6) having a source-detector distance d between 300 μm-2000 μm. The source fiber 101 is configured to be supplied with light from a light source, such as, phosphor-converted LEDs, and deliver such light to tissue 104. The detector fiber 103 is configured to pick up diffuse reflected light from tissue 104 and deliver this light to spectral analysis unit 105. As shown in FIG. 6, the DRS probe 107 consists of one source fiber 101 and one detection fiber 103, however, other suitable configurations are contemplated in accordance with the embodiments described herein. For example, in an embodiment including more than one detector fiber, the outputs from each fiber should be combined together, and the single resulting signal should be delivered into spectral analysis unit 105 where the signal is distributed over the wavelength-sensitive detectors.

According to an embodiment, the spectral analysis unit 105 is a splitter configured to distribute the received diffuse reflected light over n wavelength-sensitive photodetectors (e.g., bandpass filter+photodiode) 106, 108, 110, and 112. The spectral analysis unit 105 can include a fused fiber splitter, a dispersive splitter (e.g. prism or grating), a light guide manifold, or any suitable alternative. Detector 106 is configured to be sensitive to $\lambda 1$ having a specific full width at half maximum (FWHM1). Detector 108 is configured to be sensitive to $\lambda 2$ having FWHM2. Detector 110 is configured to be sensitive to $\lambda 3$ having FWHM3. Detector 112 is configured to be sensitive to $\lambda 4$ having FWHM4. The output of each wavelength-sensitive photodetector is input to a controller 113 having an inflammation detection unit 114. The inflammation detection unit 114 can include an algorithm which can be based on any mathematical equation on these inputs. According to an embodiment, a spectrometer or a tunable filter can also be used as a spectral detector. However, these are currently considered too expensive and/or bulky for a consumer product.

According to an example embodiment including four wavelengths, detector 106 is sensitive to $\lambda 1$ where $\lambda 1=575$ nm-585 nm, preferably 580 nm, and FWHM1=10 nm; detector 108 is sensitive to $\lambda 2$ where $\lambda 2=589$ nm-599 nm, preferably 594 nm, and FWHM2=10 nm; detector 110 is sensitive to $\lambda 3$ where $\lambda 3=670$ nm-680 nm, preferably 675 nm, and FWHM3≥10 nm; and detector 112 is sensitive to $\lambda 4$ where $\lambda 4=695$ nm-705 nm, preferably 700 nm, and FWHM4≥15 nm, preferably 20-50 nm.

According to another example embodiment including five wavelengths, detector 106 is sensitive to $\lambda 1$ where $\lambda 1=575$ nm-585 nm, preferably 580 nm, and FWHM1=10 nm; detector 108 is sensitive to $\lambda 2$ where $\lambda 2=589$ nm-599 nm, preferably 594 nm, and FWHM2=10 nm; detector 110 is sensitive to $\lambda 3$ where $\lambda 3=670$ nm-680 nm, preferably 675 nm, and FWHM3≥10 nm; detector 112 is sensitive to $\lambda 4$ where $\lambda 4=689$ nm-699 nm, preferably 694 nm, and FWHM4≥10 nm; and an additional detector (not shown) that is sensitive to $\lambda 5$ where $\lambda 5=715$ nm-725 nm, preferably 720 nm, and FWHM5≥15 nm, preferably 20-50 nm.

According to another example embodiment including five wavelengths, detector 106 is sensitive to $\lambda 1$ where $\lambda 1=570$ nm-580 nm, preferably 575 nm, and FWHM1=10 nm; detector 108 is sensitive to $\lambda 2$ where $\lambda 2=625$ nm-635 nm, preferably 630 nm, and FWHM2=10 nm; detector 110 is sensitive to $\lambda 3$ where $\lambda 3=669$ nm-679 nm, preferably 674 nm, and FWHM3≥10 nm; detector 112 is sensitive to $\lambda 4$ where $\lambda 4=737$ nm-747 nm, preferably 742 nm, and FWHM4≥10 nm; and an additional detector (not shown) that is sensitive to $\lambda 5$ where $\lambda 5=765$ nm-775 nm, preferably 770 nm, and FWHM5≥15 nm, preferably 20 nm.

Figure 5:
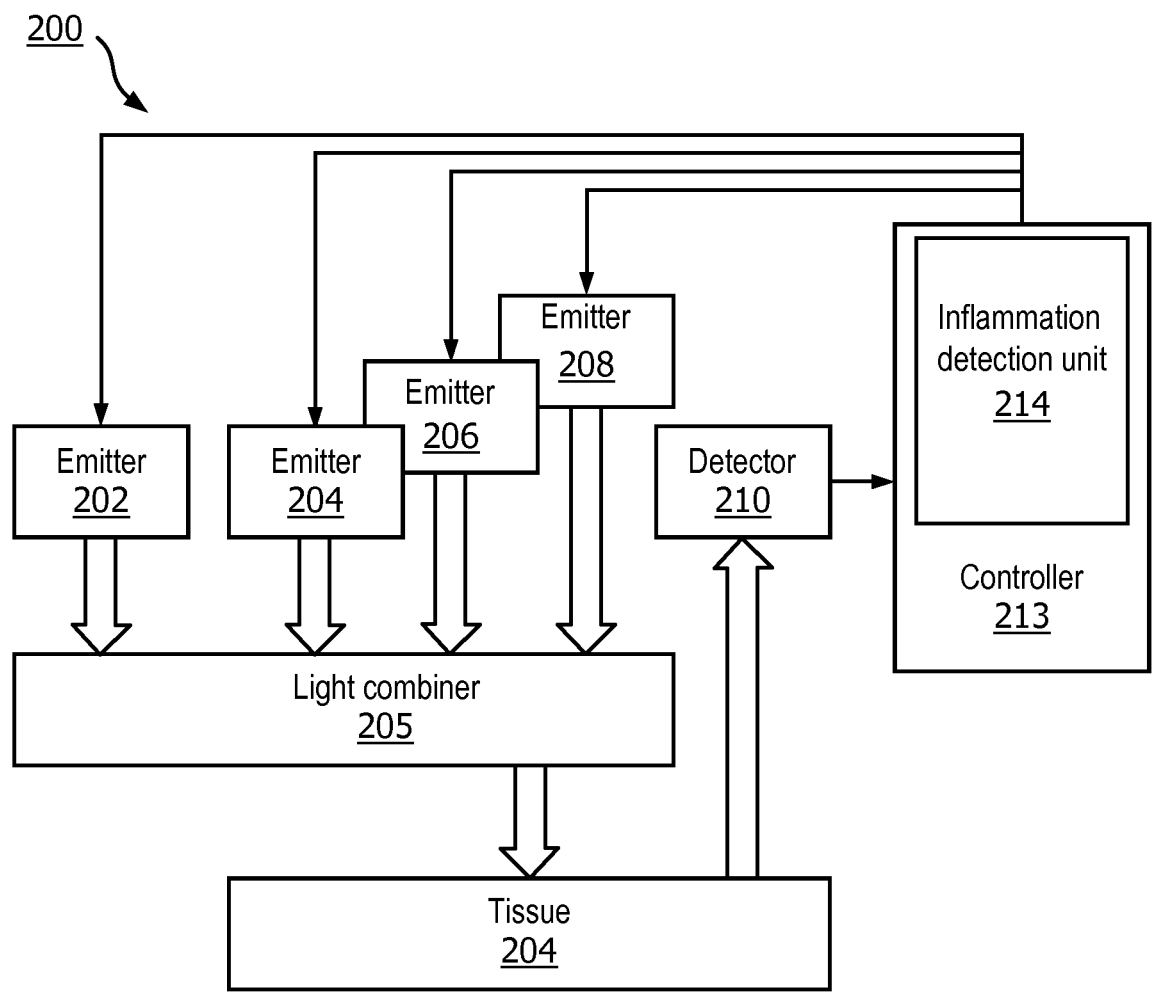
FIG. 5 is a schematic representation of a system for detecting tissue inflammation, in accordance with an embodiment.

Any of the specific wavelength selections described above can be incorporated into embodiments where the spectral diversity is provided by wavelength-specific emitters rather than wavelength-sensitive detectors. As shown in FIG. 5, an inflammation detection system 200 is shown including four wavelength-specific emitters 202, 204, 206, and 208 configured to be supplied with light from LEDs having the desired spectral properties and/or modified properties by application of, e.g., bandpass filters. Emitter 202 is associated with $\lambda 1$ and FWHM1. Emitter 204 is associated with $\lambda 2$ and FWHM2. Emitter 206 is associated with $\lambda 3$ and FWHM3. Emitter 208 is associated with $\lambda 4$ and FWHM4. Like system 100, system 200 can include additional emitters associated with additional wavelengths and bandwidths. Light from the four wavelength-specific emitters is delivered to light combiner 205 or any suitable alternative. Like system 100, system 200 includes a diffuse reflective spectroscopy (DRS) probe such as the one depicted in FIG. 6 having a source-detector distance between 300 μm-2000 μm. The detector fiber 103 is configured to pick up diffuse reflected light from tissue 204 and deliver this light to a controller 213 having an inflammation detection unit 214. The inflammation detection unit 214 can include an algorithm which can be based on any mathematical equation on these inputs.

Advantageously, the inventive systems enable accurate gingivitis detection using a minimum number of wavelengths and commercially available phosphor converted (PC) light-emitting diodes (LEDs).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for detecting inflammation in tissue, comprising:
    a light emitter configured to deliver light to gingival tissue;
    a diffuse reflective spectroscopy probe having a source-detector distance between 300 µm-2000 µm;
    a plurality of detectors configured to detect diffuse light reflected from the gingival tissue, the plurality of detectors configured to detect:
        a first wavelength that is less than 615 nm and having a first bandwidth; and
        second wavelengths greater than 615 nm and having a second bandwidth, wherein said second bandwidth is greater than said first bandwidth;
        a third wavelength greater than said second wavelength and having a third bandwidth, wherein said third bandwidth is greater than said second bandwidth; and
    a controller comprising an inflammation detection unit, said controller configured to receive input from each of the plurality of detectors for detecting tissue inflammation.

2. The system of claim 1, further comprising:
    a spectral analysis unit configured to receive and analyze detected diffuse reflected light, said spectral analysis unit comprising a splitter configured to distribute the detected light over the plurality of detectors.

3. The system of claim 1, wherein said at least second or third bandwidths are at least 50% greater than said first bandwidth.

4. The system of claim 1, wherein said at least second or third bandwidth is 100% greater than said first bandwidth.

5. The system of claim 1, wherein said at least second or third bandwidth is 100%-400% greater than said first bandwidth.

6. The system of claim 1, wherein the plurality of detectors is configured to detect at least a fourth wavelength that is greater than 615 nm, wherein said at least fourth wavelength bandwidth is greater than said first second and third bandwidths.

7. A system for detecting tissue inflammation, comprising:
    a plurality of light emitters configured to deliver light to gingival tissue;

a diffuse reflective spectroscopy probe having a source-detector distance between 300 μm-2000 μm;
a detector configured to detect diffuse light reflected from the gingival tissue, the detector configured to detect:
  a first wavelength that is less than 615 nm and having a first bandwidth; and
  second wavelength greater than 615 nm and having a second bandwidth, wherein said second bandwidth is greater than said first bandwidth;
  a third wavelength greater than said second wavelength and having a third bandwidth, wherein said third bandwidth is greater than said second bandwidth; and
a controller comprising an inflammation detection unit, said controller configured to receive input from each of the plurality of detectors for detecting tissue inflammation.

8. The system of claim 7, wherein said plurality of light emitters are configured to deliver light to a light combiner which is configured to combine the emitted light and deliver the combined light to gingival tissue.

9. The system of claim 7, wherein said at least second or third bandwidth is at least 50% greater than said first bandwidth.

10. The system of claim 7, wherein said at least second or third bandwidth is 100% greater than said first bandwidth.

11. The system of claim 7, wherein said at least second or third bandwidth is 100%-400% greater than said first bandwidth.

12. The system of claim 7, wherein the detector is configured to detect at least a fourth wavelength that is greater than 615 nm and has a fourth bandwidth, wherein said fourth bandwidth is greater than said first, second, and third bandwidths.

* * * * *